United States Patent [19]

Pose

[11] Patent Number: 4,682,584
[45] Date of Patent: Jul. 28, 1987

[54] DENTAL CARE INSTRUMENT

[76] Inventor: Wolfgang Pose, Eppendorfer Landstrasse 44, D-2000 Hamburg 20, Fed. Rep. of Germany

[21] Appl. No.: 779,129

[22] Filed: Sep. 23, 1985

[30] Foreign Application Priority Data

| Oct. 30, 1984 | [DE] | Fed. Rep. of Germany | ....... 8431762 |
| Nov. 6, 1984 | [DE] | Fed. Rep. of Germany | ....... 8432394 |
| Feb. 28, 1985 | [EP] | European Pat. Off. | ........ 85102257.4 |
| Sep. 3, 1985 | [DE] | Fed. Rep. of Germany | ....... 8525069 |

[51] Int. Cl.$^4$ ............................................. A61B 17/52
[52] U.S. Cl. ...................................... 128/1.3; 128/66; 15/167 R; 433/215
[58] Field of Search ................. 128/66, 67 A, 1.3, 1.4, 128/1.5; 433/80, 215, 229; 15/159 A, 167 R

[56] References Cited

U.S. PATENT DOCUMENTS

| 1,831,393 | 11/1931 | Pierce | .................................. 128/1.4 |
| 3,593,707 | 7/1971 | Pifer | ..................................... 128/66 |
| 4,502,497 | 3/1985 | Siahou | ............................. 15/159 A |
| 4,526,539 | 7/1985 | Blechman et al. | .................... 128/1.3 |
| 4,571,768 | 2/1986 | Kawashima | .......................... 128/1.3 |

FOREIGN PATENT DOCUMENTS 2117230 10/1983 United Kingdom ............ 15/159 A

Primary Examiner—John J. Wilson
Attorney, Agent, or Firm—Trexler, Bushnell, Giangiorgi & Blackstone, Ltd.

[57] ABSTRACT

The dental care instrument is constructed as a dentist's instrument provided with a handle, an oral spray or a toothbrush and is intended for use in intraoral magnetic field therapy with a magnetic field generator such as a permanent magnet or the like at its free end.

5 Claims, 9 Drawing Figures

Fig.1
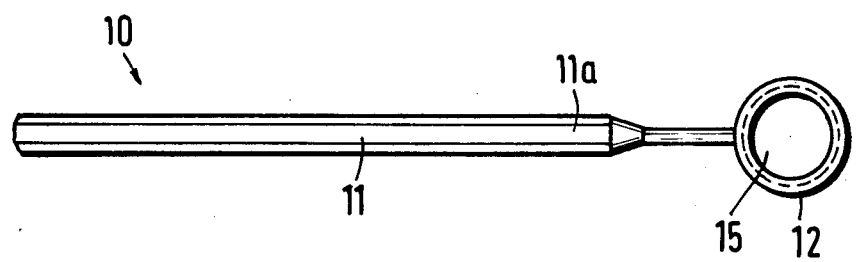
Fig.2
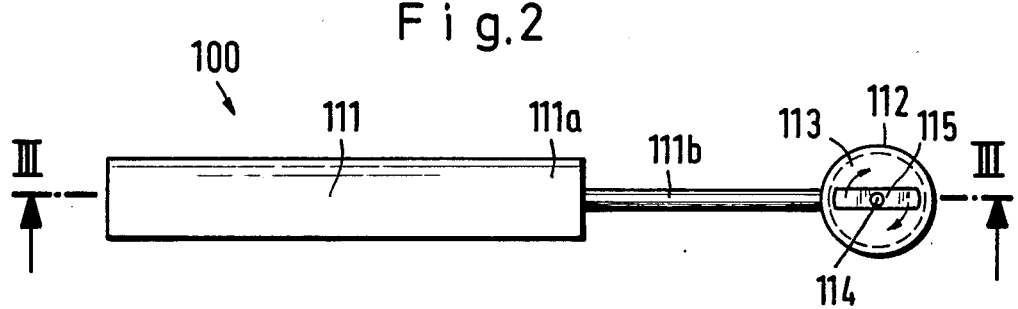
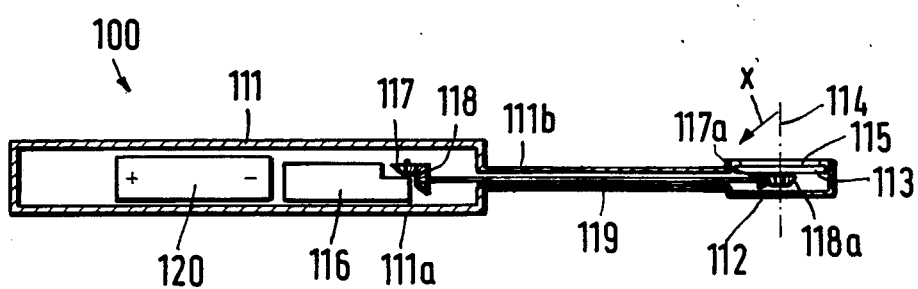
Fig.3

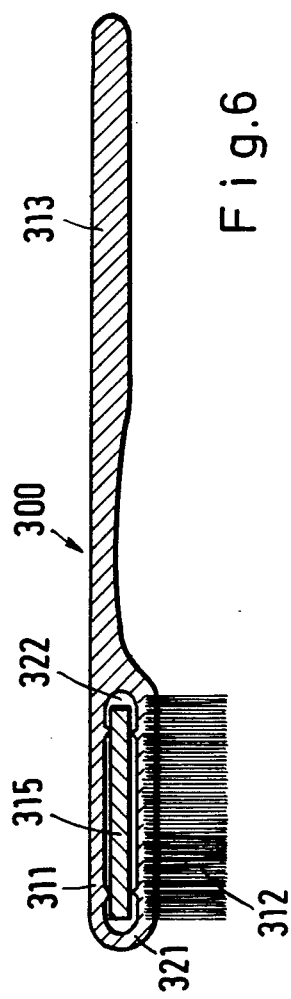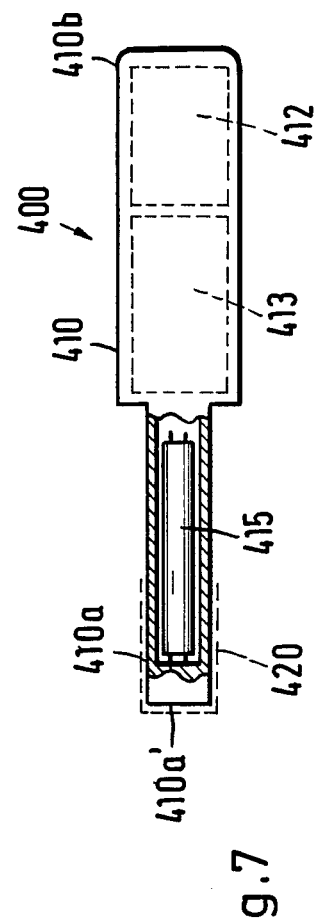

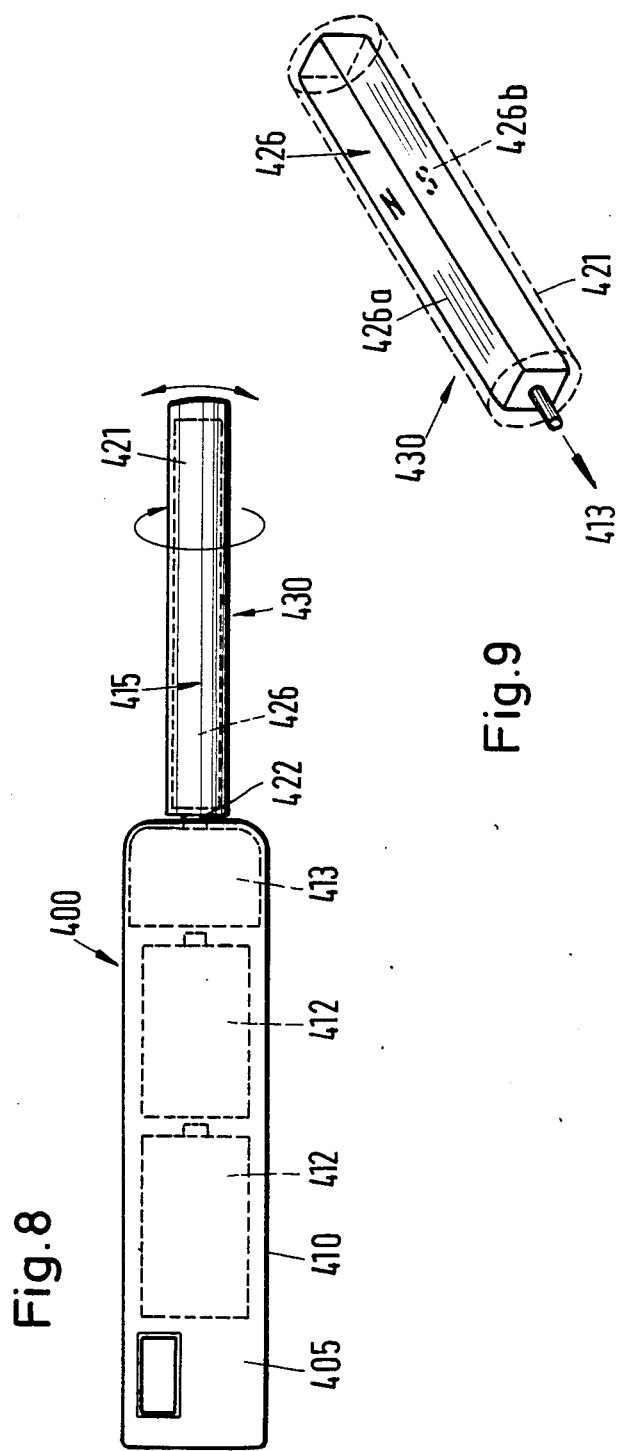

DENTAL CARE INSTRUMENT

BACKGROUND OF THE INVENTION

The present invention relates to a dental care instrument.

All elements, substances, chemical compounds, medicaments and also living organisms have their own specific, energetic-informative emission, which is either advantageous or disadvantageous to biological systems, such as man, animals and plants. This is a question of the wavelength, the polarization direction, i.e. clockwise or counterclockwise polarization and the intensity. Thus, all harmful substances, which include most dental materials, such as e.g. amalgam have specific energetic emissions, which act as harmful substance information on the body's own regulating mechanisms of biological systems and is stored by the organism. Thus, as a result of long-term action, summation and cumulation effects can occur, which can give rise to chronic-insiduous ailments with multiform symptoms.

It is known that with the most varied substances and elements, temperature changes resulting from magnetic changes of state of matter occur, which are based on an order state change linked with the magnetization change and which lead to a change in the entropy of the magnetic system. Thus, it is also known that each element and also each substance emits a specific radiation, which falls under the physical characteristics of an element, whilst the chemical characteristics of each element are also known. Each element has an energetic emission of specific wavelength, polarity and intensity. The specific radiation in radioactive elements is particularly marked and in special cases the chemical peculiarity of the element as a stable unit is completely hidden behind the physical variability, so that it must be assumed that the radiation in the case of such substances is something independent and which is detached from the chemical characteristics. Taking into account these facts, radiation therapy has been developed on the basis of magnetic field lines and the field of use thereof magnetic field therapy.

SUMMARY OF THE INVENTION

The problem of the present invention is to provide a dental care instrument which, using the intraoral magnetic field therapy, makes it possible to deactivate and/or neutralize in a simple manner the energetic harmful substance emissions of all dental materials in the mouth, such as e.g. silver or copper amalgam, silicate cements, cements for underfillings, composites, self-curing synthetic dental filling materials, root filing materials, metal alloys of all types for dental replacements, etc. which is also possible when cleaning the teeth and massaging the gums.

The present problem is solved by a dental care instrument, which, according to the invention, is constructed as a dentist's instrument, oral spray or toothbrush and which is constituted by a bar-like handle with a casing provided at one end with a magnetic field generating device arranged therein such as e.g. a fixed, rotary or oscillatory permanent magnet or electromagnet.

According to a further embodiment of the invention, the dental care instrument comprises a bar-like handle constructed as a housing, which is provided at one end with a casing, in which is arranged a disk rotatable about an axis at right angles to the longitudinal axis of the handle and with at least one bar magnet arranged thereon, which can be rotated by means of a driving arrangement driven by a battery in the handle, the disk rotating in a plane constantly variable with respect to the horizontal.

A dental care instrument constructed in this way makes it possible by intraoral magnetic field therapy to deactivate and/or neutralize energetic harmful substance emissions of all dental materials in the mouth. It has surprisingly been found that through the use of electroacupuncture in many patients, the action of a magnetic field or fields deactivates the energetic harmful substance irradiations and consequently makes them ineffective. It has also been found that on drilling out amalgam fillings after carrying out intraoral magnetic field therapy, no further harmful action occurs through the drilling dust. Possible incompatibility reactions resulting from the dental materials are eliminated and prevented by intraoral magnetic field therapy using the dental care instrument.

The invention also relates to a construction of the dental care instrument as an oral spray with a nozzle constructed as a handle for the discharge of a pulsating water jet, in which the nozzle carries an annular magnet surrounding the nozzle tube adjacent to the water jet outlet thereof. The particular advantage of this construction is that an oral spray is made readily available by the nozzle provided with an annular magnet, which not only permits cleaning of the teeth and massaging of the gums, but also enables the deactivation and/or neutralization of harmful substance emission of dental materials in the mouth. The magnetic field emitted by the annular magnet also has a positive effect on the gullet.

The invention also relates to a dental care instrument, which is constructed as a toothbrush with a bristle-carrying brush member with a shaped on, bar-like handle, the brush member being constructed as a housing in the interior of which is arranged a permanent magnet. In the same way as with the construction of the nozzle with an annular magnet of an oral spray, the dental care instrument constructed as a toothbrush with a permanent magnet provides a cleaning instrument, which not only makes it possible to clean the teeth, but in the same way to deactivate and/or neutralize harmful substance emissions of dental materials in the mouth.

The permanent magnet provided in the dental care instrument is arranged in the casing of the latter in fixed or rotary manner, the drive for the rotating permanent magnet being provided by a drive motor housed in the casing. However, the permanent magnet can also be constructed as an electromagnet.

Moreover, the dental care instrument comprises a bar-like instrument housing with a magnetic field generating means, which is constructed as a rotary permanent magnet or electromagnet, the magnetic field generator being placed in a casing portion constructed in sensor-like manner and the interior of the casing portion houses the drive motor and a power supply, such as a battery or the like. The front free end of the casing portion receiving the magnetic field generator contains a preferably washable or sterilizable mouth protection means, which is interchangeably arranged on the instrument casing.

A further solution of the problem comprises providing a dental care instrument or dentist's treatment instrument, which is constructed in such a way that in the interior of the casing of the bar-like handle, a drive motor operated by a power supply such as a battery or the like is connected to a bar-like rotor passed out of the casing of the bar-like handle, said rotor comprising a cylindrical housing, in whose interior is arranged a magnetic field generator fixed to said housing and which comprises a bar magnet constructed as a bar magnet with terminally formed north and south poles, or as a flat magnet with approximately square or rectangular cross-section and with facing surfaces constructed as north and south poles.

It is also possible to deactivate or neutralise high energy harmful substance irradiations from dental materials in the mouth by means of a treatment instrument constructed in such a way that the casing of the bar-like handle passes at one end into a sensor-like casing portion, in whose interior is arranged a bar magnet as a magnetic field generator and which is constructed as a bar magnet with terminally constructed north and south poles, or as a flat magnet with approxemately square or rectangular cross-section with facing surfaces constructed as north and south poles.

The treatment instrument can be used by introducing that part of the instrument containing the magnetic field generator into the patient's mouth, enabling a local magnetic field action to be exerted on certain teeth, but a movement of the instrument in the mouth also brings about an action of the magnetic field generated on the entire throat area, so that larger surfaces can be subject to the action of the magnetic field. However, an external application is also possible in such a way that the instrument is applied with its magnetic field generator to the cheek, jaw, etc. in the area which is to be deactivated.

Further advantageous developments of the invention can be gathered from the subclaims.

BRIEF DESCRIPTION OF THE DRAWINGS

The invention is described in greater detail hereinafter relative to non-limitative embodiments and the attached drawings, wherein show:

FIG. 1 in a view from above a bar-like dental care instrument with a magnetic field generator constructed as a permanent magnet.

FIG. 2 in a view from above, a further embodiment of the dental care instrument according to FIG. 1, but with a rotary magnet as the magnetic field generator.

FIG. 3 a vertical section along line III—III of FIG. 2.

FIG. 6 a vertical longitudinal section through a dental care instrument constructed as a toothbrush with a magnetic field generator positioned in the bristle-carrying area of the toothbrush.

FIG. 7 partly in view and partly in vertical longitudinal section, another embodiment of a dental care instrument with a magnetic field generator and an interchangeable mouth protection means arranged in the front part of the instrument.

FIG. 8 a treatment instrument with a rotating head receiving the magnetic field generator in side view.

FIG. 9 the head of a treatment instrument according to FIG. 8 constructed in sensor-like manner, with bar magnets arranged in the inner area of the head in a diagrammatic view.

DETAILED DESCRIPTION OF THE PREFERRED EMBODIMENTS

Figure 4:
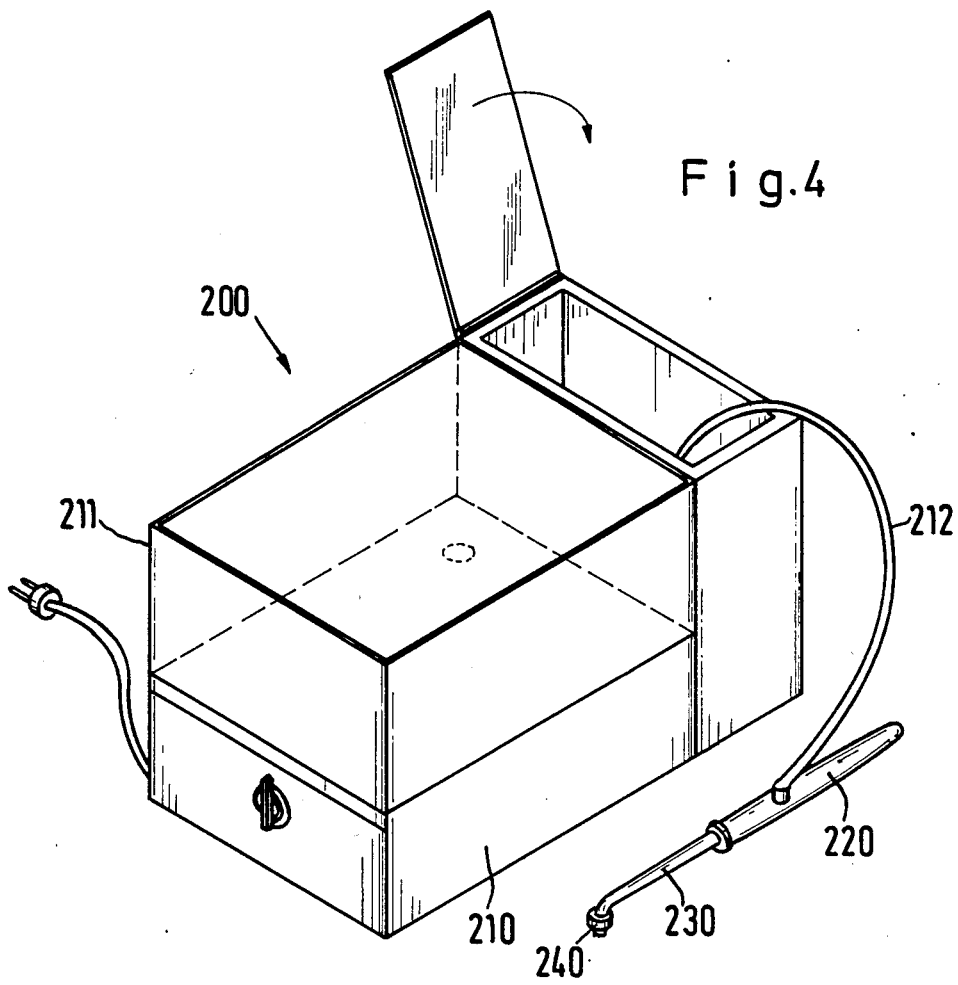
FIG. 4 a diagrammatic view of a dental care instrument constructed as an oral spray with a nozzle.

The dental care instrument 10 in FIG. 1 and which is used as a dentist's instrument, comprises a bar-like handle 3, which carries at its free end 11a an approximately disk-shaped casing 12, which can be constructed as a chromium plated brass casing in which is placed a magnetic field generator constructed as a permanent magnet. For the better handling of instrument 10, casing 12 with permanent magnet 15 is fixed by means of a tapered, bar-like portion 13 to handle 11. It is possible to construct casing 12 in such a way that the magnet 15 arranged in the interior thereof is enclosed on all sides. With such a casing construction, the casing must be constructed in such a way and made from materials such that the magnetic field lines emitted by the magnet 15 are not impaired. Advantageously the casing 12 of instrument 10 is open at one side, so that casing 12 merely comprises a support plate, to which the permanent magnet 15 is fixed. This support plate can have an all-round edge, which laterally defines the permanent magnet 15 and holds it on said plate.

Instrument 10 is used as follows. The sets of teeth slightly opened, the end of the instrument 10 carrying the permanent magnet is turned towards the chewing plane of the upper set, is moved backwards and forwards thereover in rapidly rotary movements a number of times. The instrument is then turned by 180°, so that the permanent magnet instrument is directed towards the lower set and in this position the instrument is again moved backwards and forwards several times in rapidly revolving manner over the teeth.

Whereas in the case of the instrument 10 according to FIG. 1, the permanent magnet used is fixed, in the embodiment according to FIGS. 2 and 3 a dental instrument 100 is provided, in which the instrument has at least one bar magnet, which performs rotary movements.. This instrument 100 also comprises a bar-like handle 111, which is constructed in housing-like manner and has a closable opening, so that access is obtained to the interior of the casing. At end 111a of handle 111 is provided a tapered, bar-like casing portion 111b, which carries a disk-like casing 112, in which a disk 113 is mounted in rotary manner. Disk 113 can be rotated about axis 114 by means of a driving arrangement 116 housed in the interior of handle 111. The rotary disk 113 carries at least one bar magnet 115. However, several such bar magnets can be arranged on disk 113.

The drive of disk 113 with bar magnet 115 takes place from the driving arrangement 116, via a driving shaft 119 and whilst interposing several helical gear pairs 117, 118, and 117a, 118a, driving arrangement 116 is constructed as an electromotor. The power supply for the driving arrangement is provided by a battery 120 arranged in the interior of handle 111, but it is also possible to use other power supplies for driving the electromotor of driving arrangement 116. Other driving arrangements constructed in per se known manner can also be used. Thus, for example, it is possible to use the existing compressed air for driving a correspondingly constructed driving arrangement.

The permanent magnets 15, 115 can be constructed as bar, ring or disk magnets.

The movement of disk 113 is oscillatory, i.e. the orbital plane of the disk varies constantly with respect to the horizontal. By means of a gimbal-type mounting, rotation axis 114 is constantly sloped in the direction of arrow X (FIG. 3), in such a way that the disk 113 describes a wobbling or tumbling movement. This produces an oscillating magnetic field, whose action is increased. The construction of instrument 10 has the advantage that in the case of dental treatment, often due to lack of space in the oral cavity of the patient, it is not possible to move the end of instrument 10 with the magnet. The tumbling movement of disk 113 is produced by means of a corresponding known driving arrangement and the driving shaft for disk 113 can be made elastic.

Figure 5:
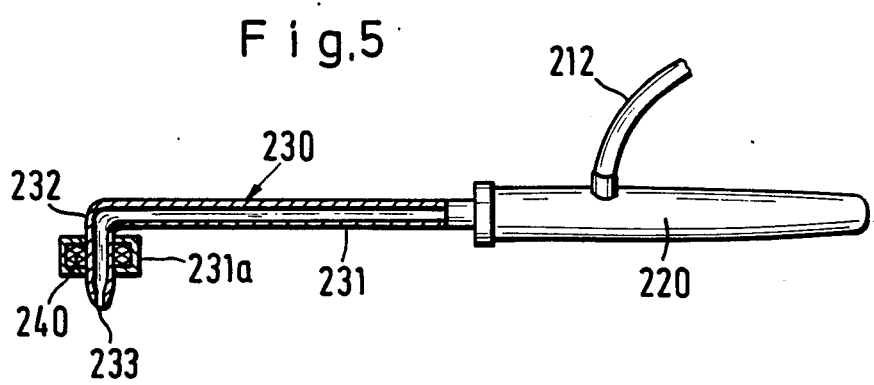
FIG. 5 a larger-scale vertical longitudinal section of the dental care instrument nozzle provided with a magnetic field generator.

The dental care instrument shown in FIG. 4 is constructed in per se known manner as an oral spray 200 and comprises an instrument casing 210, which carries a trough-like container 211, which is used for receiving the water quantity necessary for producing a pulsating water jet. This container 211 is connected to a motor-driven pump or some other suitable, pulsating water jet-producing device, not shown in the drawing and arranged in casing 210. On the pressure side, a hose 212 is connected to the pump and the end thereof is fixed to a handle 220 carrying a nozzle 230, which can be detachably connected via a plug connection to handle 220, so that nozzle 230 can be replaced when use is required by another persion and the nozzle tube 231 thereof can be bent at the end. The free end of this bent nozzle tube portion 232 then has the water jet outlet 233 (FIG. 5). The intensity of the pulsating water jet produced in the oral spray 200 can be regulated.

The oral spray functions in such a way that the water contained in container 211 can be sucked up by the pump, converted into a pulsating, i.e. pressurized water stream and the latter is supplied via hose 212 to nozzle 230, from whose opening 233 the water stream is discharged as a pulsating water jet.

The free end of the nozzle tube 231 carries adjacent to its water jet outlet 233 an annular magnet 240, constructed as a permanent magnet and which surround the nozzle tube. This annular magnet 240 can be mounted on nozzle tube 231 and can be connected thereto by means of an adhesive bond or the like. However, it is also possible when producing the generally plastic nozzle tube 231, to shape on a housing indicated at 231a in FIG. 5, which is open at one side, so that the annular magnet 240 can be mounted on inserted in casing 231a. The opening thereof is then closed so that the annular magnet 240 is surrounded by the material of nozzle tube 231 and is protected against the action of water and moisture.

The nozzle 230 constructed in accordance with the invention can be used in all electrically operated oral sprays using nozzles, as well as in the case of non-electric sprays, which can be directly connected to a water tap. In the case of such oral sprays, the force of the tap water is used for driving a turbine, which produces water hammer, i.e. a pulsating water jet.

The nozzle constructed according to the invention is used in the normal way, so that when cleaning the teeth or massaging the gums, the magnetic field produced by permanent magnet 240 simultaneously acts on the teeth. Particularly in the case of a revolving movement of the nozzle during the tooth cleaning process, a high deactivation and/or neutralization action is achieved over the teeth.

The dimensions of the annular magnet 240 used are such that completely satisfactory cleaning of the teeth is possible. Annular magnet 240 can be replaced by a plurality of individual magnets, which are then arranged in ring-like manner about the nozzle tube 231.

In the case of the toothbrush 300 of FIG. 6, it is a commercially available toothbrush, comprising a brush body 311 carrying bristles 312 and on to which is shaped a bar-like handle 313.

This brush body 311 of toothbrush 300 is constructed as a housing 321. In the interior 322 of brush body housing 321 is arranged a permanent magnet 315 which is surrounded by the housing 321.

The toothbrush 300 is made from per se known materials. It must be ensured that the housing 321 forming the brush body 311 is made from materials leading to no impairing of the magnetic field lines emitted by permanent magnet 315. The upper portion closing the interior 322 of the brush body housing 321 is constructed as a closing plate, which is then placed in interior 322 after inserting permanent magnet 315 and is fixed to the remainder of the housing.

The toothbrush 300 constructed according to the invention is used in the same way as a conventional toothbrush, so that during a cleaning movement the magnetic field emitted by permanent magnet 315 can act on the teeth. It is particularly advantageous if the toothbrush is moved backwards and forwards with a rapidly revolving motion over the teeth.

The dental care instrument shown in FIG. 5 is also used as a dentist's instrument and is designated 400, but it can also be used for taking care of the teeth.

This dental instrument 400 shown in FIG. 7 comprises a casing 410 with a magnetic field generator 415 positioned in its interior and which is constructed as a rotating permanent magnet or electromagnet. Preferably, in this embodiment, the magnetic field generator 415 is arranged in a casing portion 410 constructed in sensor-like manner. The drive motor 413 and power supply 412, whereby the latter can be a battery or the like, are arranged in the interior of the remaining casing portion 410b.

At the front free end 410a' of casing portion 410a is provided a preferably washable and/or sterilizable mouth protection means 420, which is interchangeably held by means of a circlip or some other fastening device on the instrument casing. The mouth protection means 420 comprises an e.g. cap-like part, made from suitable natural or synthetic fibre fabrics, which can be drawn on to the free end 410a' of casing portion 410a.

In all the embodiments of the dental care instrument, the magnetic field generators used can either be constructed as fixed permanent magnets, as rotary permanent magnets, or as electromagnets. However, it is also possible to use differently constructed means for producing a magnetic alternating field.

Such dental care instruments make it possible to deactivate and/or neutralize the energetic emissions of harmful substances of all types. All elements, substances, chemical compounds, medicaments, etc. and also living organisms have their own specific, energetic-informative emission, which either has a favourable or an unfavourable action on biological systems (human—animals—plants). It is a question of the wavelengths, the polarizations direction, i.e. clockwise or counterclockwise polarisation and the intensity. All so-called harmful substances, which include most dental materials, such as e.g. amalgam, have specific energetic emissions, which act as harmful substance information on the body's own regulating mechanisms of biological systems and which are stored by the organism. Summation and cumulation effects occur during long-term action, and these can be looked upon as the cause of chronic-insiduous ailments with multiform symptoms. With the aid of electroacupuncture according to Dr. Voll (EAV), it is possible to establish after the action of magnetic fields of all the dental materials in the mouth, that the energetic harmful substance emissions have been deactivated and consequently made ineffective. Voll electroacupunctrure is a diagnosis method for detecting extraneous substances in the body, i.e. those substances which although leaving behind traces are scarcely detectable. In testing, working takes place with electromagnetic frequencies or involuted substances which are enclosed in ampoules. These ampoules are in the circuit between the patient's hand, the investigator's electrode and the resistance measuring instrument. As the substances have different wavelengths in the ampoule, as a function of the substance type, as such electromagnetic oscillations pass through the glass wall of the ampoule, they pass via energy paths to the organ. Individual skin points have special relationships to the organs. If the frequency of the ampoule content corresponds to the toxic substance frequencies in the organ, then there is an interference of the oscillations which can be read from an ohmmeter scale and is further expressed by the immediate reduction in the tenderness at such a point. These processes can be reproduced at all times. Thus, EAV is able to detect toxic substances, where laboratory medicine fails, because the latter normally investigates the flowing blood at which the toxic substances have already disappeared, because they have been deposited in the organ. Through the use of the dental care instrument, it is possible to deactivate the harmful substances of the dental materials in the mouth, the deactivation obtained being detectable by the EAV test.

When using such dental care instruments, the particular advantage is that not only is dental care possible, but also a deactivation of dental materials.

In the case of a treatment instrument 400 according to FIG. 8, a drive motor 413 operated by means of a power supply, such as a battery or the like 412 is arranged in the interior of the casing 410 of the bar-like handle 405 and its drive shaft is connected to a bar-like rotor 430 passed out of the casing 410 of the bar-like handle 405. This rotor comprises a cylindrical housing 421, in whose inner area is arranged a magnetic field generator 415 fixed to the housing 421. The housing 421 of rotor 430 is made from plastic or suitable materials not impairing the magnetic field generated. In this embodiment of the treatment instrument according to FIG. 8, the magnetic field generator 415 is a bar magnet, which can be terminally provided with north and south poles. In the case of the embodiment shown in FIG. 9, said bar magnet is constructed as a flat magnet 426 with approximately square or rectangular cross-section, the facing longitudinal faces 426a,426b being constructed as a north or south pole. In the longitudinal edge region, said flat magnet 426 ist rounded, so that in said region there is contact with the inner wall surface of the cylindrical housing 421 of rotor 430, so that whenn the dimensions are appropriately chosen, flat magnet 426 is held firmly in the inner area of rotor housing 421. Magnet 426 is secured in the inner area of housing 421 by using moulding materials such as plastics and similar materials not impairing the magnetic field generated in the interior of the housing. However, it is also possible to use adhesive bonds.

In order to bring about an oscillating movement of the magnetic field generator 415 in rotor 430, the latter is connected by means of an elastic shaft in portion 422 in FIG. 8 to the drive shaft of drive motor 413. On putting drive motor 413 into operation, instead of rotor 430 rotating about its median longitudinal axis, its free end performs a movement about the central longitudinal axis, so that an oscillating movement is obtained.

What is claimed is:

1. A dental care instrument comprises a bar-like handle configured in the form of a housing, part of said housing having an elongate handle and another portion of said housing having a chamber, a magnet arranged in a position in said chamber such that when the part of the housing that contains said chamber and said magnet is inserted into an oral cavity and given a predetermined movement the magnet will produce a magnetic field to neutralize energy emissions from substances in said oral cavity, characterized in that a rotating disk is arranged on an axis at a right angle to the lengthwise dimension of said handle, said magnet comprises at least one bar magnet on said disk, and driving means by which the aforesaid disk may be rotated in a plane which can be continuously modified with respect to the horizontal.

2. A dental care instrument according to claim 1 further characterized in that said driving means is in said housing.

3. A dental care instrument according to claim 1 further characterized in that said last-named means includes a mounting for the disk such that rotation of the disk causes the magnet to produce an oscillating magnetic field.

4. A dental care instrument according to claim 1 including a power supply for said driving means, said power supply being in said housing.

5. A dental care instrument according to claim 1 further characterized in that said last-named means includes a drive motor, a drive shaft in said handle, and mechanically coupling said drive shaft to said motor.

* * * * *